United States Patent
Mallett et al.

(10) Patent No.: US 9,442,173 B2
(45) Date of Patent: Sep. 13, 2016

(54) NMR ASSESSMENT SYSTEM AND METHOD

(75) Inventors: Michael John Disney Mallett, Lower Hutt (NZ); Gianni Mario Ferrante, Mede (IT)

(73) Assignees: HTS—110 LIMITED, Lower Hutt (NZ); STELAR s.r.l., Mede (IT)

( * ) Notice: Subject to any disclaimer, the term of this patent is extended or adjusted under 35 U.S.C. 154(b) by 910 days.

(21) Appl. No.: 13/700,302

(22) PCT Filed: May 27, 2011

(86) PCT No.: PCT/NZ2011/000088
§ 371 (c)(1),
(2), (4) Date: Mar. 14, 2013

(87) PCT Pub. No.: WO2011/149367
PCT Pub. Date: Dec. 1, 2011

(65) Prior Publication Data
US 2013/0176028 A1    Jul. 11, 2013

(30) Foreign Application Priority Data

May 28, 2010 (NZ) ........................ 585753

(51) Int. Cl.
*G01R 33/383* (2006.01)
*G01N 24/08* (2006.01)
*G01R 33/563* (2006.01)

(52) U.S. Cl.
CPC ............ *G01R 33/383* (2013.01); *G01N 24/08* (2013.01); *G01N 24/085* (2013.01); *G01R 33/56383* (2013.01)

(58) Field of Classification Search
CPC .......... G01R 33/383; G01R 33/56383; G01N 24/08; G01N 24/085
See application file for complete search history.

(56) References Cited

U.S. PATENT DOCUMENTS

| | | | |
|---|---|---|---|
| 3,419,793 A | 12/1968 | Genthe et al. | |
| 4,514,691 A * | 4/1985 | De Los Santos | G01V 3/14 324/301 |
| 5,055,787 A | 10/1991 | Kleinberg et al. | |
| 5,168,224 A * | 12/1992 | Maruizumi | G01N 23/04 324/300 |
| 6,029,080 A * | 2/2000 | Reynnells | A01K 45/00 356/52 |
| 6,268,727 B1 | 7/2001 | King et al. | |
| 6,479,994 B1 | 11/2002 | Hills et al. | |
| 6,668,403 B2 * | 12/2003 | Seufert | A61B 6/0471 378/209 |
| 6,759,601 B1 * | 7/2004 | Petty | G01G 9/00 177/1 |
| 6,946,838 B2 * | 9/2005 | Corver | G01N 24/085 324/306 |
| 7,002,346 B2 * | 2/2006 | Schaepman | G01K 7/42 177/50 |
| 7,008,486 B2 * | 3/2006 | Corver | G01R 33/28 134/1 |

(Continued)

FOREIGN PATENT DOCUMENTS

| | | |
|---|---|---|
| WO | 2004104599 | 12/2004 |
| WO | 2007144206 | 12/2007 |

*Primary Examiner* — Dixomara Vargas
(74) *Attorney, Agent, or Firm* — Dann, Dorfman, Herrell and Skillman, P.C.

(57) ABSTRACT

A system for NMR assessing a sample or a series of samples in turn which comprises means for applying a static magnetic field in a first direction through the sample, prepolarizing means for first applying a magnetic field in substantially the same direction to the sample, means for applying an alternating excitation magnetic field in a second different direction through the sample, means for sensing energy emitted by the sample in response to the excitation magnetic field, and means arranged to provide an indication of an assessment of the sample based on the energy emitted by the sample in response to the excitation magnetic field.

17 Claims, 6 Drawing Sheets

(56) References Cited

U.S. PATENT DOCUMENTS

| | | | | |
|---|---|---|---|---|
| 7,015,693 B2* | 3/2006 | Corver | ................ | G01N 24/085 324/300 |
| 7,041,914 B2* | 5/2006 | Aptaker | .................. | G01G 9/00 177/1 |
| 7,061,239 B2* | 6/2006 | McKendry | ........... | G01R 33/389 324/307 |
| 7,064,548 B2* | 6/2006 | Aptaker | ........... | G01R 33/34046 324/318 |
| 7,084,627 B2* | 8/2006 | McKendry | ............. | G01G 9/005 324/307 |
| 7,199,581 B2* | 4/2007 | Corver | ................... | G01N 24/08 324/307 |
| 8,588,362 B1* | 11/2013 | Rogers | .................... | A61B 6/03 378/114 |
| 2005/0116712 A1 | 6/2005 | Corver et al. | | |
| 2005/0242809 A1 | 11/2005 | McKendry et al. | | |
| 2005/0242813 A1 | 11/2005 | Aptaker et al. | | |

* cited by examiner

NMR ASSESSMENT SYSTEM AND METHOD

FIELD OF INVENTION

The invention relates to an improved system and method for nuclear magnetic resonance (NMR) assessing a sample or series of samples, particularly moving samples. More particularly but not exclusively the invention relates to the use of NMR for check weighing moving products on a production line particularly products in containers or otherwise packaged.

BACKGROUND OF INVENTION

Check weighing systems are used for example in quality control of products on a production line to ensure that each container (or other package) contains a required amount of product. For example check weighing is used by the pharmaceuticals industry for monitoring and regulation of the amount of a drug sealed in glass vials. The drug weight can be as small as a fraction of a gram, and must be weighed with an accuracy of a few percent or better, in a vial weighing tens of grams and at a rate of several weighings per second.

International patent application publication WO 99/67606 discloses a check weighing apparatus and method for check weighing products in such applications using NMR.

SUMMARY OF INVENTION

In broad terms in one aspect the invention comprises a system for NMR assessing a sample or a series of samples in turn which comprises: means for applying a static magnetic field in a first direction through the sample; pre-polarising means for first applying a magnetic field in substantially the same direction to the sample; means for applying an alternating excitation magnetic field in a second different direction through the sample; means for sensing energy emitted by the sample in response to the excitation magnetic field; and means arranged to provide an indication of an assessment of the sample based on the energy emitted by the sample in response to the excitation magnetic field.

In broad terms in another aspect the invention comprises a system for NMR assessing a sample or a series of samples in turn moving through an interrogation zone, comprising:
scanning magnet arranged to apply a magnetic field for creating a magnetisation within a sample in an interrogation zone;
pre-polarising magnet arranged to apply a magnetic field in substantially the same direction to the sample prior to location of the sample in the interrogation zone;
means for applying a pulse of alternating magnetic field in a different direction through the interrogation zone for temporarily changing the magnetisation of the sample in the interrogation zone;
means for sensing energy emitted by the sample as the magnetisation of the sample returns to its original state and for outputting a signal in dependence thereon.

In broad terms in a further aspect the invention comprises method for NMR assessing a sample or a series of samples in turn moving through an interrogation zone, comprising:
applying a magnetic field for creating a magnetisation within a sample in an interrogation zone;
applying a magnetic field in substantially the same direction to the sample prior to location of the sample in the interrogation zone;
applying a pulse of alternating magnetic field in a different direction through the interrogation zone to temporarily change the magnetisation of the sample in the interrogation zone;
sensing energy emitted by the sample as the magnetisation of the sample returns to its original state and outputting a signal in dependence thereon.

The field strength of the pre-polarising magnet may be greater than that of the scanning magnet. In at least some embodiments the pre-polarising magnet means has a field strength of between one and four times greater than the field strength of the scanning magnet. In at least some embodiments the pre-polarising magnet has a field strength which is effective to, in the time for which the sample is exposed to the pre-polarising field, polarise the sample to about the equilibrium polarisation of the scanning magnet. In at least some embodiments the pre-polarising magnet has a field strength which is effective to, in the time for which the sample is exposed to the pre-polarising field, polarise the sample to an extent (which may be greater than equilibrium polarisation of the scanning magnet and for example 1, 2, 3, or 4 times greater) such that between the pre-polarising magnet and the interrogation zone the magnetisation of the sample relaxes to not less than about 95% or 100% of about the equilibrium polarisation of the scanning magnet.

In at least some embodiments the field strength of the pre-polarising magnet is variable and the system comprises a control system with feedback to the pre-polarisation magnet indicative of the polarisation state of the sample and arranged to vary the pre-polarising field strength. In at least some embodiments the field strength of the pre-polarising magnet is variable and the system comprises a control system arranged to vary the strength of the pre-polarising field with change in the moving speed of the samples between the pre-polarising magnet and the interrogation zone, or with change of the T1 NMR relaxation time of the samples.

The system may also comprise means for storing predetermined calibration data for at least one similar sample such as a sample of known mass, which calibration data relates the sample such as the mass of the at least one similar sample to the corresponding signal output by said sensing means; and means for comparing the signal output by said sensing means with said calibration data to provide an indication of the mass of the sample.

In broad terms in a further aspect the invention comprises a magnet system for NMR assessing a moving sample or a series of sample which comprises a first pre-polarising magnet arranged to apply a magnetic field to the sample(s) as the samples move past or through the pre-polarising magnet and a second NMR scanning magnet arranged to apply a magnetic field to the samples in substantially the same direction as the samples move past or through the scanning magnet after the pre-polarising magnet, the field strength of the second magnet being of a sufficient strength for NMR analysis of the samples.

The pre-polarising magnet and the scanning magnet may be physically integrated together, and may comprise toroidal magnets with a common passage through both magnets through which samples may move.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

BRIEF DESCRIPTION OF THE FIGURES

The invention is further described with reference to the accompanying drawings by way of example and without intending to be limiting, in which.

DETAILED DESCRIPTION OF EMBODIMENTS

Figure 1:
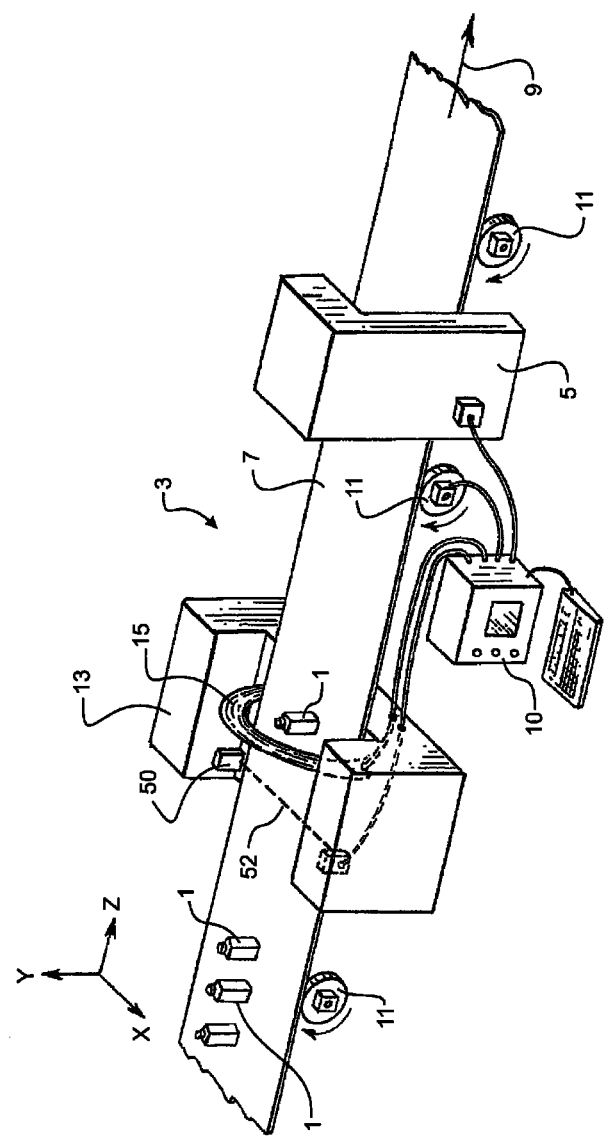
FIG. 1 shows an NMR check weighing system on a production line.

FIG. 1 shows part of a production line which check weighs the product content of containers 1 and in particular shows a proposed prior art weighing station 3 which uses magnetic resonance techniques provided 'in-line' for weighing each of the filled containers. The system also includes a reject station 5, which removes those containers from the line which do not contain a required amount of product content within predetermined limits. As shown, the containers 1 are transported to the weighing station 3 from a filling and sealing station (not shown) by a conveyor 7 which, as represented by arrow 9, moves in the z direction through the action of the rotating conveyor wheels 11.

NMR is used to determine the mass of the sample or product within each of the containers 1. The containers in this embodiment are of glass because they do not give off an MR signal which might interfere with the measurement process. In this embodiment, the weighing station 3 comprises a permanent magnet 13, an RF coil 15 and a computer control system 10. The magnet 13 is used to create a homogeneous DC or static magnetic field in the x direction across the direction of movement of the products. The sample in each glass container contains nuclei which each possess a magnetic moment e.g. $^1$H nuclei (protons). This magnetic moment is a result of the spin of the nuclei. The magnetic moment acts like a small bar magnet and its strength is dependent on the type of nuclei. Before the sample is placed in the static magnetic field, the individual nuclear magnetic moments are randomly orientated. When they enter the static magnetic field, they tend to align with the static field, along with x-direction in this case. The magnetic moments can align themselves either parallel or anti-parallel to the static field. Alignment parallel to the static field is the lower energy state and thus more of the magnetic moments adopt this orientation. This results in the sample having a resultant net macroscopic magnetisation parallel to the static field.

The nuclei possess spin and as a result, they rotate or precess around the static magnetic field at the Larmor frequency (which is dependent on the strength of the static magnetic field). Applying an AC magnetic field to the sample at the sample's Larmor frequency and orientated orthogonal to the static magnetic field will cause the sample's net magnetisation to rotate about the AC magnetic field's axis, away from the direction of the static field. This magnetic field is generated by applying a corresponding AC current to the RF coil 15. The angle of rotation of the net magnetisation can be varied by varying the amount of energy delivered to the RF coil 15. In the embodiment shown, an excitation field which causes a 90° rotation is used to excite the sample. A pulse of AC excitation current is applied to the RF coil 15, of a frequency equal to the Larmor frequency of the sample under test in the static magnetic field. The excitation current flowing through the RF coil 15 generates a corresponding magnetic field in the z-direction. This excitation magnetic field causes the net magnetisation of the sample in the container 1 to rotate or precess about the z-axis at the Larmor frequency. When the excitation current is removed from the RF coil 15, the nuclei in the sample begin to relax back to their equilibrium positions; emitting RF energy at the Larmor frequency as they do so. This induces a signal in the RF coil 15, which decays exponentially. The peak amplitude of the signal induced in the RF coil 15 by the sample is directly proportional to the number of magnetic moments in the sample. After the 90° pulse has been applied to the sample, the sample is left in a high-energy, non-equilibrium state, from which it will relax back to its equilibrium state and hence the number of molecules in the sample. The received signal is then passed to the computer control system 10 which assesses the amplitude of the signal received from the unknown sample to obtain an indication of the mass (or weight) of the sample being tested. The control system may be arranged to compare the peak signal level with calibration data obtained by testing a similar sample or samples of known mass, to provide an indication of the mass of the sample currently being tested. The calibration data may be obtained from a number of similar samples of different known masses during a calibration routine before the production batch is begun and is stored in memory. The calibration data may be a function which relates the peak amplitude of the MR signal received from the sample under test to the mass of the sample. If the control system determines that the mass of the current sample being analysed is not the required mass within a given tolerance, it outputs a control signal to the reject station 5, causing the reject station to remove the current container 1 being tested from the conveyor when it arrives at the reject station 5.

Such a system can be used to determine the weight or mass of most samples or products provided they contain an MR responsive element in a known amount relative to the other elements in the sample. Since the hydrogen nucleus, or proton, is the element which gives the largest MR signal, due to it possessing the strongest magnetic moment, it is the one most often used. Other isotopes which have nuclear spin and will therefore provide an MR signal include: certain isotopes of nitrogen, phosphorus, sodium, potassium, fluorine and carbon and oxygen. If the check weighing station 3 described above is to be able to determine the mass of various samples using the MR signals from different MR responsive elements, then the control system must store calibration data for each of the different samples. It must also be able to generate and receive signals at the different Larmor frequencies needed to be able to excite the different MR responsive elements.

It takes a finite period of time after the sample enters the static field generated by the magnet 13 for the net magnetisation of the sample to develop along the x-direction. If the excitation signal is applied to the RF coil 15 before the magnetisation has fully developed, then the strength of the signal generated by the sample will not be at its maximum.

The net magnetisation and thus the strength of the resultant signal produced by the sample varies with time in the static magnetic field. A disadvantage of a system described above is that the minimum period of time after the sample enters the static field generated by the magnet 13 for the net magnetisation of the sample to develop along the x-direction, is a limiting factor on the speed at which the samples can progress through the weighing station 3 and/or the length in the x-direction of the static field magnet 13 must be increased which adds cost.

Figure 2:
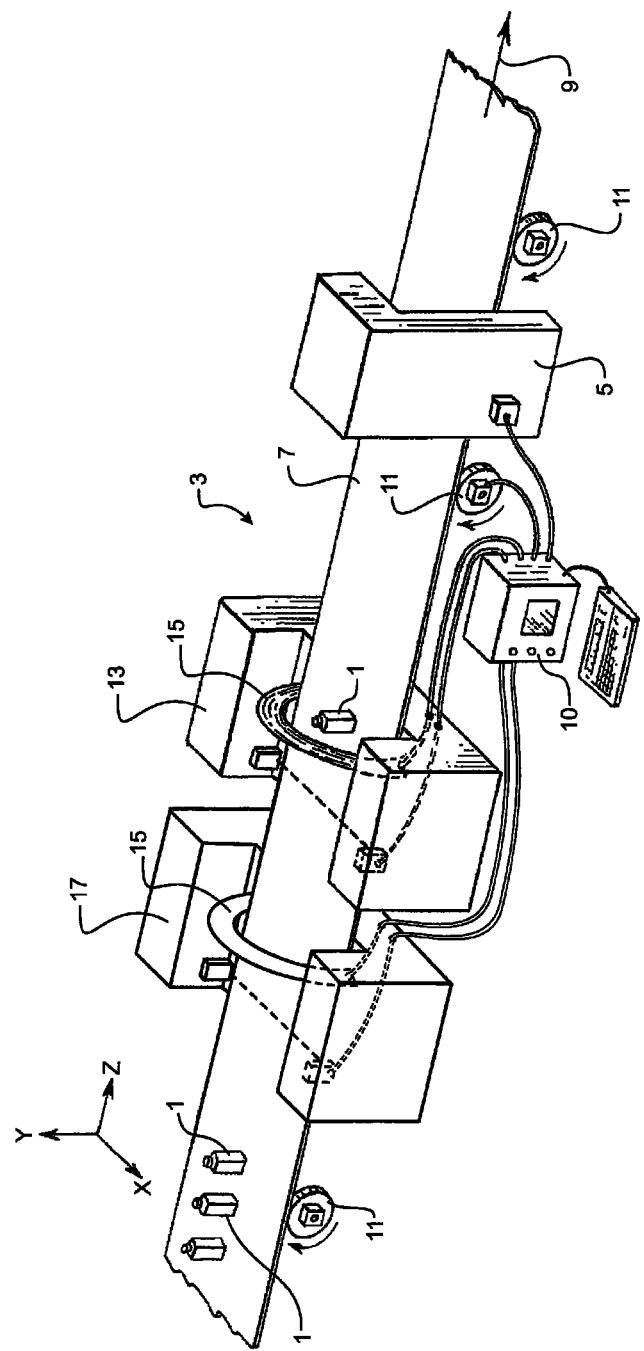
FIG. 2 shows one embodiment of an NMR check weighing system of the invention on a production line.

FIG. 2 shows part of a production line with a weighing station 3 of the invention. Many elements of the check weighing station of FIG. 2 are the same as those of the check weighing station of FIG. 1 and unless indicated otherwise similar reference numerals in FIG. 2 indicate similar components as in the check weighing station of FIG. 1. Generally before the check weighing system uses magnetic resonance techniques for 'in-line' for weighing filled containers 1.

In accordance with the invention, in the system of FIG. 2 a pre-polarising magnet 17 is arranged to apply a magnetic field to the samples in substantially the same direction to the static magnet 13 (sometimes hereinafter referred to as the scanning or measurement magnet), to pre-polarise the samples to at least some extent, prior to the samples reaching the interrogation zone.

The pre-polarising magnet 17 thus reduces the time subsequently required for the samples in the field of the scanning magnet 13 for the nuclear magnetic polarisation of the samples to reach ~100% of the scanning magnet's equivalent total polarisation. Preferably the pre-polarising magnet 17 has a field strength which is effective in the time for which the sample is exposed to the pre-polarising field i.e. the time taken for the samples to pass the pre-polarising magnet 17 on the conveyor 7, to polarise the sample to about the equilibrium polarisation of the scanning magnet.

The field strength of the pre-polarising magnet 17 may be greater than that of the scanning magnet 13. For example the pre-polarising magnet 17 may have a field strength of between one and four times greater than the field strength of the scanning magnet 13. The pre-polarising magnet 17 may have a field strength which is effective in the time for which the sample is exposed to the pre-polarising field, to polarise the samples to an extent such that between the pre-polarising magnet 17 and the magnet 13, the magnetisation of the sample relaxes to not less than about 95% of the equilibrium polarisation of the scanning magnet, and most preferably not less than about the equilibrium polarisation of the scanning magnet. The pre-polarising magnet may be arranged to polarise the sample to a value greater than the 100% of the equilibrium polarisation of the scanning magnet. The pre-polarising magnet may have a magnetic field strength relative to that of the scanning magnet such that the ratio of the two magnetic fields is dependent upon the $T_1$ of the sample and the transit time of the sample through the magnet system. A faster transit time or a longer $T_1$ will require a higher pre-polarising field strength.

The pre-polarising magnet 17 may be a fixed field magnet(s), or a variable field magnet(s) (see further below), and/or may be mounted on a carriage such that the spacing between the pre-polarising and measuring magnets can be adjusted i.e. the pre-polarising magnet is at a variable distance from the scanning magnet. The distance between the pre-polarising magnet and the scanning magnet may then be set such that the polarisation of the samples until they reach the scanning magnet is to a desired level and preferably to ~100% of the equilibrium polarisation of the scanning magnet.

The pre-polarising magnet 17 and scanning magnet 13 may each comprise one or more superconducting magnets, copper electromagnets, or permanent magnets.

Systems of the invention may be useful for assessing and in particular weighing samples which are in solid form, powder form, liquid form, gas form, or any mixture.

As stated the pre-polarising magnet may be arranged to polarise the nuclear magnetic spins within the samples to a value of ~100% of the equivalent total polarisation of a field equal to that of the scanning magnet, as the samples move in either a continuous or stop-go motion through the magnet system. The relative polarisation due to NMR longitudinal relaxation (T1) is given by $$M_Z(t) = M_{Z,eq} - [M_{Z,eq} - M_Z(0)]e^{-t/T1}$$

The absolute polarisation is proportional to the field strength so we require $$B^{PM} \times M_Z^{PM}(t) = B^{SM} \times M_{z,eq}^{SM}$$

Where $B^{PM}$ is the field of the pre-polarising magnet, $B^{SM}$ is the field of the scanning magnet, $M_Z^{PM}(t)$ is the relative polarisation achieved within the pre-polarizing magnet after a time (t) and $M_{z,eq}^{SM}$ is the relative equilibrium polarisation achieved within the scanning magnet.

Therefore $$B^{PM} = B^{SM}/(1 - e^{-t/T1})$$

Where t is the time the sample spends in the pre-polarising field and is inversely proportional to the line speed.

Limits $$t/T1 \to \infty, B^{PM} \sim B^{SM}$$

$$T/T1 \to 0, B^{PM} \cdot B^{SM}/(t/T1)$$

Figure 3:
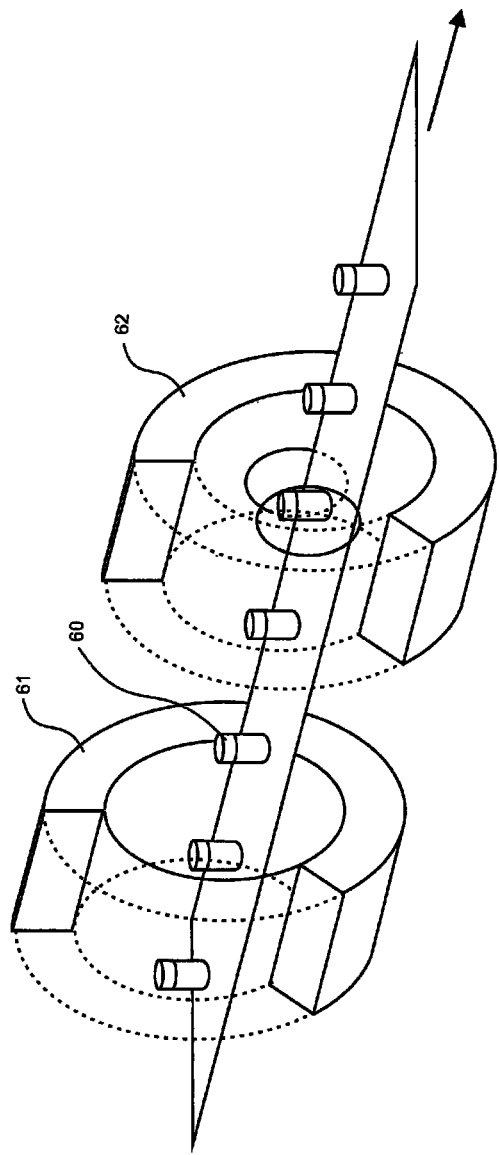
FIG. 3 shows another more general embodiment of an NMR check weighing system of the invention.

FIG. 3 more generally illustrates the principle of operation of systems of the invention. Moving samples are indicated at 60. The samples move past or through pre-polarising magnet 61. The samples then subsequently move past or through scanning or measuring magnet 62 of an NMR measuring system. In the pre-polarising magnet 61 the samples are pre-polarised to at least some extent and preferably to about 100% (or more) of polarisation achieved in the subsequent NMR scanning magnet 62. The pre-polarising magnet may have a greater field strength than the field strength of the scanning magnet 62. For example, if the scanning magnet 62 has a field strength of approximately 1 T then the pre-polarising magnet 61 may have a field strength of approximately 3 T to increase the net magnetisation of the samples to preferably approximately 100% of sample magnetisation achieved in the scanning magnet, in the time in which the samples pass the pre-polarising magnet. Highest accuracy/repeatability of the NMR measurement is achieved where the pre-polarising magnet creates an equilibrium polarisation level (~99-101%) in the sample for the scanning magnet to analyse. This is achieved by matching the magnetic field strength of the pre-polarising magnet to the NMR relaxation time (T1) and the transit time of the samples.

Figure 4A:
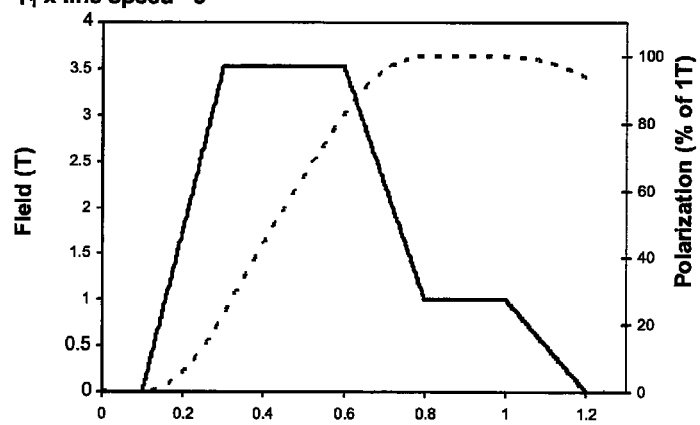
FIG. 4 shows how the pre-polarising field strength in an NMR system of the invention may be varied dependent on speed of movement, or change of T1 NMR relaxation time of the samples under analysis.
Figure 4B:
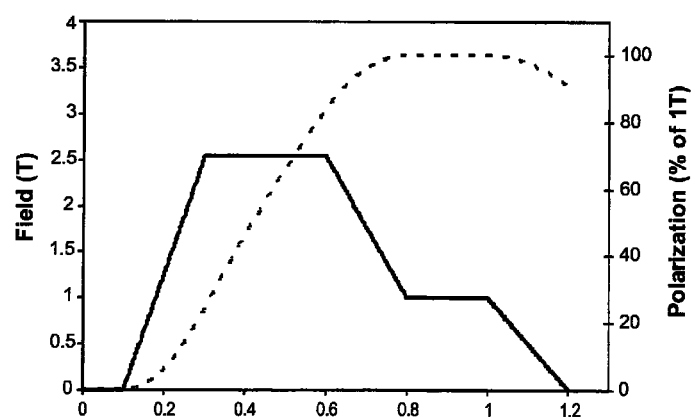
Figure 4C:
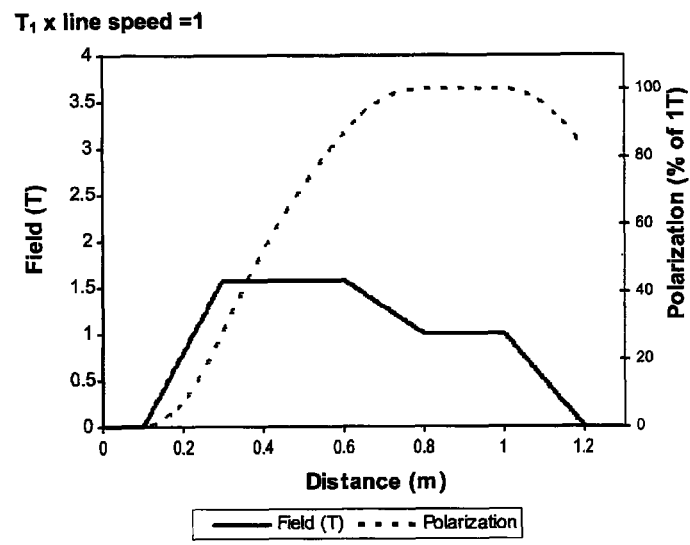
Figure 4D:
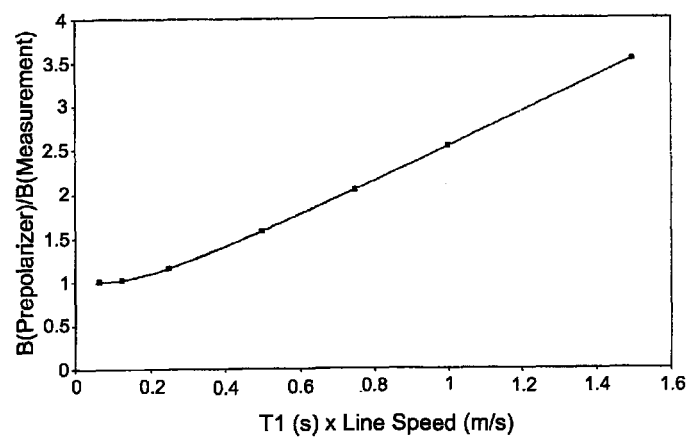

In some embodiments the field strength of the pre-polarising magnet may be variable. The system may comprise a control system with feedback to the pre-polarisation magnet indicative of the polarisation state of the samples and arranged to vary the pre-polarising field strength. The system may comprise a control system arranged to vary the strength of the pre-polarising field with change in the moving speed of the samples between the pre-polarising magnet and the scanning magnet. With a variable pre-polarising magnetic field strength, the field strength may be controlled by the control system dependant on the longitudinal NMR relaxation time ($T_1$) of the samples and the speed of sample transit through the magnet system. In preferred embodiments a feedback circuit is arranged to monitor the transit speed of the samples and to adjust the strength of the magnetic field of the pre-polarising magnet to ensure that ~100% polarisation is achieved regardless of transit speed. This is illustrated by FIG. 4. The measuring field is fixed at 1 T. To compensate for either a change in line speed or sample T1, the pre-polarising field is varied to achieve 99.9% polarisation in the measuring magnet. If the sample is moving relatively quickly then the field strength of the pre-polarising magnet may be higher as indicated in FIG. 4a, to relatively rapidly magnetise the sample towards 100% polarisation in the relatively short time which the sample passes through the pre-polarising magnet. Referring to FIG. 4c, if the sample is moving at a relatively slower speed, so that the sample will be exposed to the pre-polarising field for a relatively longer time, then the strength of the pre-polarising field may be lower. FIG. 4b illustrates an intermediate scenario. FIG. 4d shows the pre-polarising field strength as a function of T1 and line speed.

Figure 5A:
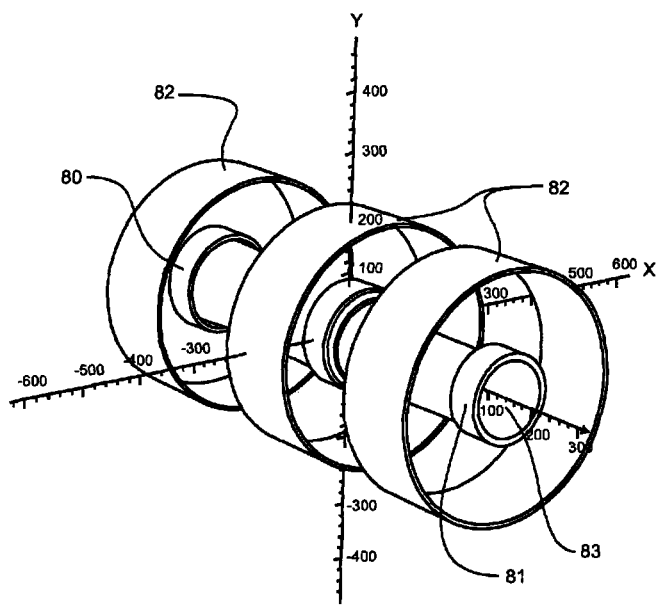
FIG. 5 shows an embodiment of an integrated pre-polarising and measuring magnets of an NMR assessment system of the invention.
Figure 5B:
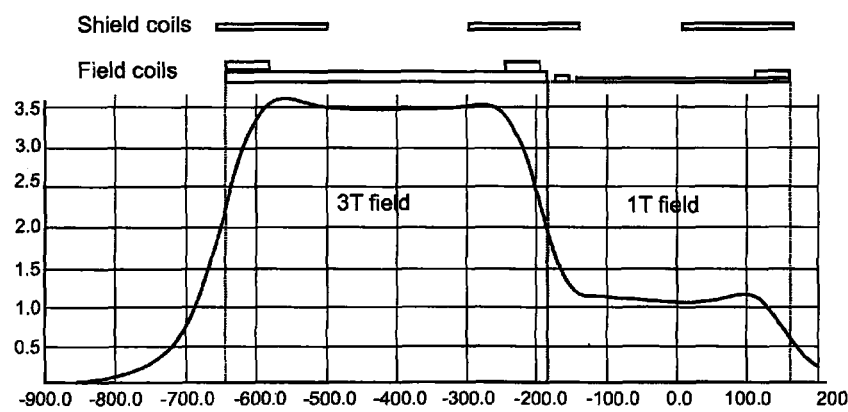

FIG. 5a shows a magnet embodiment comprising integrated pre-polarising and measuring magnets. The magnet comprises a pre-polarising solenoid 80 and a lower field strength measuring solenoid 81. The pre-polarising magnet and the scanning magnet are physically integrated together, and comprise toroidal magnets with a common passage 83 through both magnets through which samples may move. The magnet may also comprise three active shield coils 82 and a number of small field correction coils. FIG. 5b graphically shows the field strength (y axis) and by way of example the comparative time for which samples are exposed to the two fields (x axis).

The description of systems of the invention above particularly with reference to FIGS. 2 to 4 describe systems for check weighing but in other embodiments the system may be arranged to assess or measure the ratios of two or more components in the samples in the containers, to carry out NMR spectroscopy on the samples for quality control or quality analysis purposes, or to assess some other quality of the samples. In the embodiments above the samples are in containers such as glass containers but the samples or products may be in any other suitable form of container or package and in other embodiments the samples may be un-packaged where qualities of the samples are being assessed before placement of the samples in a container or package. In the embodiments described the samples are moving on a conveyor of a production line but the invention may have application other than in relation to a production line, for assessing moving samples such as assessing unused products which have been in the field or in use for some time but are unopened, as to the weight amount remaining or a quality aspect of the product.

Although the invention has been described by way of example and with reference to particular embodiments, it is to be understood that modifications and/or improvements may be made without departing from the scope or spirit of the invention.

The invention claimed is:

1. A system for NMR assessing a sample or a series of samples in turn moving through an interrogation zone, comprising:

a scanning magnet arranged to apply a static magnetic field for creating a magnetisation within a sample in an interrogation zone;

an RF coil arranged to apply a pulse of alternating magnetic field in a different direction through the interrogation zone for temporarily changing the magnetisation of the sample in the interrogation zone;

a conveyor for transporting the sample, or series of samples in turn, in a machine direction through the interrogation zone;

a pre-polarising magnet before the interrogation zone in the machine direction, arranged to apply a magnetic field in substantially the same direction as the static magnetic field to the sample prior to location of the sample in the interrogation zone, with a field strength which is variable to a maximum greater than that of the scanning magnet, and which is effective in the time for which the sample is exposed to the pre-polarising field, to polarise the sample to an extent such that between the pre-polarising magnet and the interrogation zone the magnetisation of the sample relaxes to not less than about 95% of equilibrium polarisation by the scanning magnet; and means for sensing energy emitted by the sample as the magnetisation of the sample returns to its equilibrium state and for outputting a signal in dependence thereon.

2. A system according to claim 1 wherein the conveyor comprises a belt-based conveyor.

3. A system according to claim 1 wherein the pre-polarising magnet has a field strength which is effective to in the time for which the sample is exposed to the pre-polarising field, polarise the sample to about the equilibrium polarisation of the scanning magnet.

4. A system according to claim 1 wherein the system comprises a control system with feedback to the pre-polarisation magnet indicative of the polarisation state of the sample and arranged to vary the pre-polarising field strength.

5. A system according to claim 1 wherein the system comprises a control system arranged to vary the strength of the pre-polarising field with change in the moving speed of the samples between the pre-polarising magnet and the interrogation zone.

6. A system according to claim 1 wherein the pre-polarising magnet means has a field strength of between one and four times greater than the field strength of the scanning magnet.

7. A system according to claim 1 arranged to provide an indication of weight of the sample based on said output signal.

8. A system according to claim 1 arranged to provide an indication of component ratios in the sample based on said output signal.

9. A system according to claim 1 arranged to provide an indication of a quality of the sample based on said output signal.

10. A system according to claim 1 arranged to store predetermined calibration data for at least one similar known sample, which calibration data relates the at least one similar sample to the corresponding signal output by said sensing means; and arranged to compare said output signal with said calibration data to provide an assessment of the sample.

11. A magnet system for NMR assessing a moving sample or a series of sample which comprises a conveyor for conveying the sample or series of samples in a machine direction, a first pre-polarising magnet arranged to apply a magnetic field to the sample(s) as the samples move past or through the pre-polarising magnet, and a second NMR scanning magnet arranged to apply a magnetic field to the samples in substantially the same direction as the samples move past or through the scanning magnet after the pre-polarising magnet, the field strength of the pre-polarising magnet being variable to a maximum greater than that of the scanning magnet, and which is effective in the time for which the sample is exposed to the pre-polarising field, to polarise the sample to an extent such that between the pre-polarising magnet and the interrogation zone the magnetisation of the sample relaxes to not less than about 95% of equilibrium polarisation by the scanning magnet, the field strength of the second magnet being of a sufficient strength for NMR analysis of the samples.

12. A magnet system according to claim 11 wherein the conveyor is a belt-based conveyor.

13. A magnet system according to claim 12 wherein the pre-polarising magnet and the scanning magnet are toroidal magnets with a common passage through both magnets through which samples may move.

14. A magnet system according to claim 11 wherein the pre-polarising magnet and the scanning magnet are physically integrated together.

15. A magnet system according to claim 11 wherein the field strength of the pre-polarising magnet is greater than that of the scanning magnet.

16. A magnet system according to claim 11 wherein the pre-polarising magnet means has a field strength of between one and four times greater than the field strength of the scanning magnet.

17. A magnet system according to claim 11 wherein the pre-polarising magnet has a field strength which is effective to in the time for which the sample is exposed to the pre-polarising field, polarise the sample to equilibrium polarisation of the scanning magnet.

* * * * *